United States Patent
Levin et al.

(10) Patent No.: US 6,313,123 B1
(45) Date of Patent: Nov. 6, 2001

(54) ACETYLENIC SULFONAMIDE THIOL TACE INHIBITORS

(75) Inventors: Jeremy I. Levin, New City, NY (US); James M. Chen, Stoddard Court, NJ (US)

(73) Assignee: American Cyanamid Company, Madison, NJ (US)

( * ) Notice: Subject to any disclaimer, the term of this patent is extended or adjusted under 35 U.S.C. 154(b) by 0 days.

(21) Appl. No.: 09/492,974

(22) Filed: Jan. 27, 2000

Related U.S. Application Data

(60) Provisional application No. 60/155,218, filed on Jan. 27, 1999.

(51) Int. Cl.[7] .................. A61K 31/5375; A61P 19/02; C07D 295/13
(52) U.S. Cl. .................. 514/238.2; 544/159; 544/160; 564/89
(58) Field of Search .................. 544/159, 160; 564/89; 514/238.2

(56) References Cited

U.S. PATENT DOCUMENTS

| | | |
|---|---|---|
| 5,455,258 | 10/1995 | MacPherson et al. . |
| 5,506,242 | 4/1996 | MacPherson et al. . |
| 5,552,419 | 9/1996 | MacPherson et al. . |
| 5,753,653 | 5/1998 | Bender et al. . |
| 5,770,624 | 6/1998 | Parker . |
| 5,804,593 | 9/1998 | Warpechoski et al. . |
| 5,817,822 | 10/1998 | Nantermet et al. . |
| 5,929,097 | 7/1999 | Levin et al. . |

FOREIGN PATENT DOCUMENTS

| | | |
|---|---|---|
| 606 046 | 12/1993 | (EPX) . |
| 757 037 | 7/1996 | (EPX) . |
| 757 984 | 8/1996 | (EPX) . |
| 803 505 | 4/1997 | (EPX) . |
| WO 95/35275 | 12/1995 | (WOX) . |
| WO 95/35276 | 12/1995 | (WOX) . |
| WO 96/00214 | 1/1996 | (WOX) . |
| WO 96/27583 | 9/1996 | (WOX) . |
| WO 96/33172 | 10/1996 | (WOX) . |
| WO 97/18194 | 5/1997 | (WOX) . |
| WO 97/19068 | 5/1997 | (WOX) . |
| WO 97/20824 | 6/1997 | (WOX) . |
| WO 97/22587 | 6/1997 | (WOX) . |
| WO 97/27174 | 7/1997 | (WOX) . |

(List continued on next page.)

OTHER PUBLICATIONS

Shire, M.D., Exp. Opin. Ther. Patents 8(5), 531 (1998).
Grossman, J.M., Women's Health, 6(6), 627 (1997).
Isomaki, P.J., Ann. Med., 29, 499 (1997).
Camussi, G., Drugs, 55(5), 613 (1998).
Mathison et al., J. Clin. Invest. 81, 1925, (1988).
Miethke et. al., J. Exp. Med., 175, 91 (1992).
Piquet, P.F., J. Exp. Med. 166, 1280 (1987).
Beuther, B., Ann. Rev., Biochem, 57, 505 (1988).
Ksontini, R., Arch, Surg., 133, 558, (1998).
Packer, M., Circulation, 92(6), 1379 (1995).
Ferrari, R., et al., Circulation 92(6), 1479 (1995).
Hotamisligil, G.S. et al., Science, 259, 87 (1993).
Peterson, P.K. et al., J. Clin. Invest., 89, 574 (1992).
Pallares–Trujillo et al., Med. Res. Reviews, 15(6), 533 (1995).
Old, L., Science, 230,630 (1985).
Rankin, E.C. et al., Br. J. Rheumatol., 34, 334 (1995).
McGeehan et al., Current Pharmaceutical Design, 2, 662 (1996).
Script 20, 2349 (1998).
MacPherson et al., J. Med. Chem., 40, 2525 (1997).
Tamura et al., J. Med. Chem. 41, 640 (1998).
Levin et al., Bioorg. & Med. Chem Letters, 8, 2657 (1998).
Pikul et al., J. Med. Chem., 41, 3568 (1998).

*Primary Examiner*—Robert W. Ramsuer
(74) *Attorney, Agent, or Firm*—John W. Hogan, Jr.

(57) ABSTRACT

The compounds of formula B:

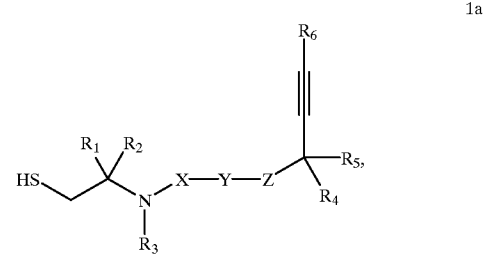

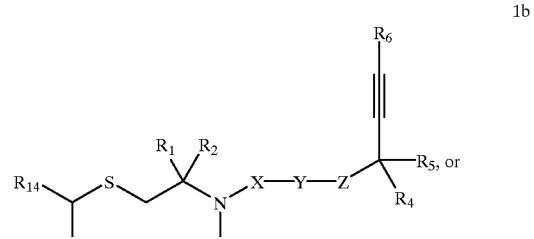

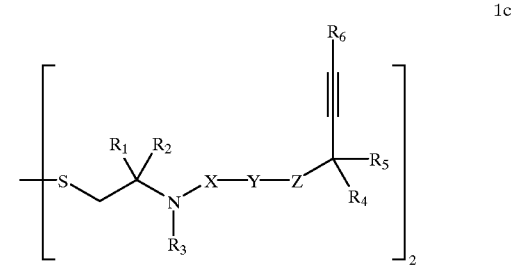

which are useful in disease conditions mediated by TNF-α, such as rheumatoid arthritis, osteoarthritis, sepsis, AIDS, ulcerative colitis, multiple sclerosis, Crohn's disease and degenerative cartilage loss

13 Claims, No Drawings

FOREIGN PATENT DOCUMENTS

| | | |
|---|---|---|
| WO 97/45402 | 12/1997 | (WOX) . |
| WO 98/03164 | 1/1998 | (WOX) . |
| WO 98/03166 | 1/1998 | (WOX) . |
| WO9803164 | 1/1998 | (WOX) . |
| WO 98/07697 | 2/1998 | (WOX) . |
| WO 98/08815 | 3/1998 | (WOX) . |
| WO 98/08822 | 3/1998 | (WOX) . |
| WO 98/08823 | 3/1998 | (WOX) . |
| WO 98/08825 | 3/1998 | (WOX) . |
| WO 98/08827 | 3/1998 | (WOX) . |
| WO 98/08853 | 3/1998 | (WOX) . |
| WO 98/16503 | 4/1998 | (WOX) . |
| WO 98/16506 | 4/1998 | (WOX) . |
| WO 98/16514 | 4/1998 | (WOX) . |
| WO 98/16520 | 4/1998 | (WOX) . |
| WO 98/27069 | 6/1998 | (WOX) . |
| WO 98/31664 | 7/1998 | (WOX) . |
| WO 98/.33768 | 8/1998 | (WOX) . |
| WO 98/34918 | 8/1998 | (WOX) . |
| WO 98/39313 | 9/1998 | (WOX) . |
| WO 98/39329 | 9/1998 | (WOX) . |
| WO 98/42659 | 10/1998 | (WOX) . |
| WO 98/43963 | 10/1998 | (WOX) . |
| 1 9542189 | 5/1997 | (DEX) . |

ACETYLENIC SULFONAMIDE THIOL TACE INHIBITORS

This application claims the benefit of U.S. Provisional Application No. 60/155,218, filed Jan. 27, 1999.

FIELD OF INVENTION

This invention relates to acetylenic aryl sulfonamide thiols which act as inhibitors of TNF-α converting enzyme (TACE). The compounds of the present invention are useful in disease conditions mediated by TNF-α, such as rheumatoid arthritis, osteoarthritis, sepsis, AIDS, ulcerative colitis, multiple sclerosis, Crohn's disease and degenerative cartilage loss.

BACKGROUND OF THE INVENTION

TNF-α converting enzyme (TACE) catalyzes the formation of TNF-α from membrane bound TNF-α precursor protein. TNF-α is a pro-inflammatory cytokine that is believed to have a role in rheumatoid arthritis [Shire, M. G.; Muller, G. W. Exp. Opin. Ther. Patents 1998, 8(5), 531; Grossman, J. M.; Brahn, E. J. Women's Health 1997, 6(6), 627; Isomaki, P.; Punnonen, J. Ann. Med. 1997, 29, 499; Camussi, G.; Lupia, E. Drugs, 1998, 55(5), 613.] septic shock [Mathison, et. al. J. Clin. Invest. 1988, 81, 1925; Miethke, et. al. J. Exp. Med. 1992, 175, 91.], graft rejection [Piguet, P. F.; Grau, G. E.; et. al. J. Exp. Med. 1987, 166, 1280.], cachexia [Beutler, B.; Cerami, A. Ann. Rev. Biochem. 1988, 57, 505.], anorexia, inflammation [Ksontini, R,; MacKay, S. L. D.; Moldawer, L. L. Arch. Surg. 1998, 133, 558.], congestive heart failure [Packer, M. Circulation, 1995, 92(6), 1379; Ferrari, R.; Bachetti, T.; et. al. Circulation, 1995, 92(6), 1479.], post-ischaemic reperfusion injury, inflammatory disease of the central nervous system, inflammatory bowel disease, insulin resistance [Hotamisligil, G. S.; Shargill, N. S.; Spiegelman, B. M.; et. al. Science, 1993, 259, 87.] and HIV infection [Peterson, P. K.; Gekker, G.; et. al J. Clin. Invest. 1992, 89, 574; Pallares-Trujillo, J.; Lopez-Soriano, F. J. Argiles, J. M. Med. Res. Reviews, 1995, 15(6), 533.]], in addition to its well-documented antitumor properties [Old, L. Science, 1985, 230, 630.]. For example, research with anti-TNF-α antibodies and transgenic animals has demonstrated that blocking the formation of TNF-α inhibits the progression of arthritis [Rankin, E. C.; Choy, E. H.; Kassimos, D.; Kingsley, G. H.; Sopwith, A. M.; Isenberg, D. A.; Panayi, G. S. Br. J. Rheumatol. 1995, 34, 334; Pharmaprojects, 1996, Therapeutic Updates 17 (October), au197-M2Z.]. This observation has recently been extended to humans as well as described in "TNF-α in Human Diseases", Current Pharmaceutical Design, 1996, 2, 662.

It is expected that small molecule inhibitors of TACE would have the potential for treating a variety of disease states. Although a variety of TACE inhibitors are known, many of these molecules are peptidic and peptide-like which suffer from bioavailability and pharmacokinetic problems. In addition, many of these molecules are non-selective, being potent inhibitors of matrix metalloproteinases and, in particular, MMP-1. Inhibition of MMP-1 (collagenase 1) has been postulated to cause joint pain in clinical trials of MMP inhibitors [Scrip, 1998, 2349, 20] Long acting, selective, orally bioavailable non-peptide inhibitors of TACE would thus be highly desirable for the treatment of the disease states discussed above.

U.S. Pat. Nos. 5,455,258, 5,506,242, 5,552,419, 5,770,624, and 5,817,822 as well as European patent application EP606,046A1 and WIPO international publications WO9600214 and WO9722587 disclose non-peptide inhibitors of matrix metalloproteinases and/or TACE of which the aryl sulfonamide hydroxamic acid shown below is representative. Additional publications disclosing sulfonamide based MMP inhibitors which are variants of the sulfonamide-hydroxamate shown below, or the analogous sulfonamide-carboxylates, are European patent applications EP-757037-A1 and EP-757984-A1 and WIPO international publications WO9535275, WO9535276, WO9627583, WO9719068, WO9727174, WO9745402, WO9807697, WO9831664, WO9833768, WO9839313, WO9839329, WO9842659 and WO9843963. The discovery of this type of MMP inhibitor is further detailed by MacPherson, et. al. in J. Med. Chem., (1997), 40, 2525 and Tamura, et. al. in J. Med. Chem. (1998), 41, 640.

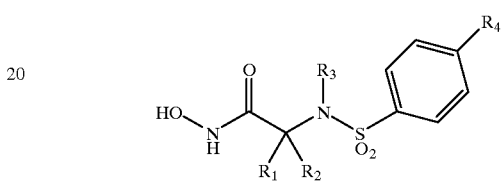

Publications disclosing β-sulfonamide-hydroxamate inhibitors of MMPs and/or TACE in which the carbon alpha to the hydroxamic acid has been joined in a ring to the sulfonamide nitrogen, as shown below, include U.S. Pat. No. 5,753,653, WIPO international publications WO9633172, WO9720824, WO9827069, WO9808815, WO9808822, WO9808823, WO9808825, WO9834918, WO9808827, Levin, et. al. Bioorg. & Med. Chem. Letters 1998, 8, 2657 and Pikul, et. al. J. Med. Chem. 1998, 41, 3568.

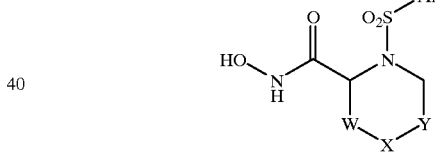

The patent applications DE19,542,189-A1, WO9718194, and EP803505 disclose additional examples of cyclic sulfonamides as MMP and/or TACE inhibitors. In this case the sulfonamide-containing ring is fused to a aromatic or heteroaromatic ring.

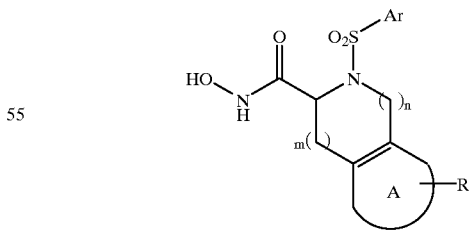

Examples of sulfonamide hydroxamic acid MMP/TACE inhibitors in which a 2 carbon chain separates the hydroxamic acid and the sulfonamide nitrogen, as shown below, are disclosed in WIPO international publications WO9816503, WO9816506, WO9816514 and WO9816520 and U.S. Pat. No. 5,776,961.

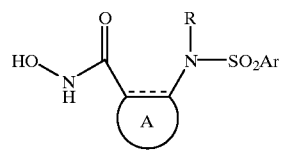

Analogous to the sulfonamides are the phosphinic acid amide hydroxamic acid MMP/TACE inhibitors, exemplified by the structure below, which have been disclosed in WIPO international publication WO9808853.

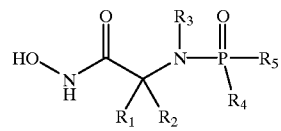

Sulfonamide MMP/TACE inhibitors in which a thiol is the zinc chelating group, as shown below, have been disclosed in WIPO international application 9803166.

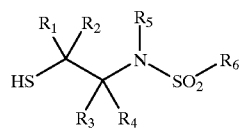

It is an object of this invention to disclose aryl sulfonamide hydroxamic acid MMP/TACE inhibitors in which the sulfonyl aryl group is para-substituted with a substituted butynyl moiety or a propargylic ether, amine or sulfide.

SUMMARY OF THE INVENTION

The invention provides TACE and MMP inhibitors having the formula:

B wherein B is

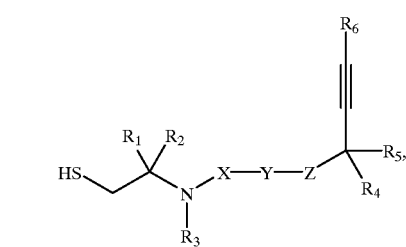

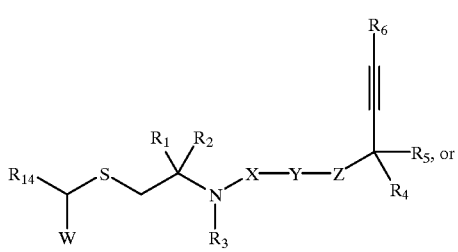

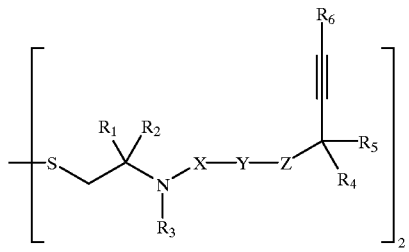

wherein:

W is oxygen or sulfur;

X is $SO_2$ or $—P(O)—R_{10}$;

Y is aryl or heteroaryl as defined below, with the proviso that X and Z may not be bonded to adjacent atoms of Y;

Z is O, NH, $CH_2$ or S;

$R_1$ is hydrogen, aryl, alkyl of 1–6 carbon atoms, alkenyl of 2–6 carbon atoms, alkynyl of 2–6 carbon atoms;

$R_2$ is hydrogen, aryl or heteroaryl as defined below, cycloalkyl of 3–6 carbon atoms, —C4–C8-cycloheteroalkyl, alkyl of 1–6 carbon atoms, alkenyl of 2–6 carbon atoms, alkynyl of 2–6 carbon atoms, or $CONR_8R_9$;

or $R_1$ and $R_2$, together with the atom to which they are attached, may form a ring wherein $R_1$ and $R_2$ represent a divalent moiety of the formula:

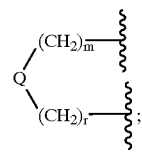

wherein

Q=a carbon-carbon single or double bond, O, S, SO, $—N—R_{11}$, or $—CONR_{15}$;

m=1–3;

r=1 or 2, with the proviso that when Q is a bond, r is equal to 2;

Aryl is phenyl or naphthyl optionally substituted by one to two substituents selected from $R_7$, where $R_7$ is as defined below;

Heteroaryl is defined as

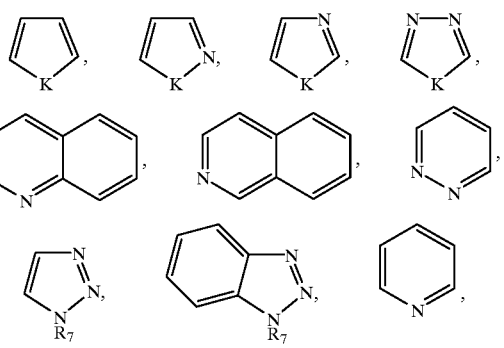

-continued

[Structures shown: benzimidazole, indazole-type, quinoxaline, indole, isoquinoline, pyrimidine (or), pyrazine — each with K as heteroatom position]

optionally mono- or di- substituted by $R_7$, wherein K is defined as O, S or —$NR_{15}$;

$R_3$ is hydrogen or alkyl of 1–6 carbon atoms;

or $R_1$ and $R_3$, together with the atoms to which they are attached, may form a 5 to 8 membered ring wherein $R_1$ and $R_3$ represent divalent moieties of the formulae:

[Two divalent moiety structures shown with $(CR_{12}R_{13})_s$, $(CR_{12}R_{13})_m$ attached to Q; and $(CR_{12}R_{13})_u$, $(CR_{12}R_{13})_m$ attached to ring A]

wherein

Q and m are as defined above;

A is aryl or heteroaryl;

s is 0–3;

u is 1–4;

$R_4$ and $R_5$ are each, independently, hydrogen, alkyl of 1–6 carbon atoms, —CN, —CCH;

$R_6$ is hydrogen, aryl, heteroaryl, alkyl of 1–6 carbon atoms, alkenyl of 2–6 carbon atoms, alkynyl of 2–6 carbon atoms, cycloalkyl of 3–6 carbon atoms or —C4–C8-cycloheteroalkyl as defined below;

$R_7$ is hydrogen, halogen, alkyl of 1–6 carbon atoms; alkenyl of 2–6 carbon atoms; alkynyl of 2–6 carbon atoms, cycloalkyl of 3–6 carbon atoms, —$OR_8$, —CN, —$COR_8$, perfluoroalkyl of 1–4 carbon atoms, —O-perfluoroalkyl of 1–4 carbon atoms, —$CONR_8R_9$, —$S(O)_nR_8$, —$OPO(OR_8)OR_9$, —$PO(OR_8)R_9$, —$OC(O)NR_8R_9$, —$C(O)NR_8OR_9$, —$COOR_8$, —$SO_3H$, —$NR_8R_9$, —$N[(CH_2)_2]_2NR_8$, —$NR_8COR_9$, —$NR_8COOR_9$, —$SO_2NR_8R_9$, —$NO_2$, —$N(R_8)SO_2R_9$, —$NR_8CONR_8R_9$, —$NR_8C(=NR_9)NR_8R_9$, —$NR_8C(=NR_9)N(C=OR_8)R_9$, —$NR_8C(=NR_9)N(SO2R_8)R_9$, tetrazol-5-yl, —$SO_2NHCN$, —$SO_2NHCONR_8R_9$, phenyl, heteroaryl as defined above, or —C4–C8-cycloheteroalkyl as defined below;

wherein —$NR_8R_9$ may form a pyrrolidine, piperidine, morpholine, thiomorpholine, oxazolidine, thiazolidine, pyrazolidine, piperazine, or azetidine ring;

wherein —C4–C8-cycloheteroalkyl is defined as

[Various cycloheteroalkyl ring structures shown with K and $R_{15}$ substituents]

wherein K is defined as above;

$R_8$ and $R_9$ are each, independently, hydrogen, alkyl of 1–6 carbon atoms, cycloalkyl of 3–6 carbon atoms, aryl, heteroaryl or —$C_5$–$C_7$-cyclohetero-alkyl;

$R_{10}$ is alkyl of 1–6 carbon atoms, cycloalkyl of 3–6 carbon atoms, aryl or heteroaryl as defined above;

$R_{11}$ is hydrogen, alkyl of 1–6 carbon atoms, cycloalkyl of 3–6 carbon atoms, aryl, heteroaryl, —$S(O)_nR_8$, —$COOR_8$, —$CONR_8R_9$, —$SO_2NR_8R_9$ or —$COR_8$;

$R_{12}$ and $R_{13}$ are independently selected from H, —$OR_8$, —$NR_8R_9$, alkyl of 1–6 carbon atoms, alkenyl of 2–6 carbon atoms, alkynyl of 2–6 carbon atoms, cycloalkyl of 3–6 carbon atoms, aryl, heteroaryl, —$COOR_8$; —$CONR_8R_9$; or $R_{12}$ and $R_{13}$ together form a —$C_3$–$C_6$-cycloalkyl of 3–6 carbon atoms or a —C4–C8-cycloheteroalkyl ring; or $R_{12}$ and $R_{13}$, together with the carbon to which they are attached, form a carbonyl group;

with the proviso that $R_{10}$ and $R_{12}$ or $R_{11}$ and $R_{12}$ may form a cycloheteroalkyl ring, wherein cycloheteroalkyl is as defined above, when they are attached to adjacent atoms;

$R_{14}$ is —$OR_8$, —$NR_8R_9$, alkyl of 1–6 carbon atoms, cycloalkyl of 3–6 carbon atoms, aryl or heteroaryl;

$R_{15}$ is hydrogen, aryl, heteroaryl, alkyl of 1–6 carbon atoms or cycloalkyl of 3–6 carbon atoms;

and n is 0–2;

or a pharmaceutically acceptable salt thereof.

The invention is further directed to a process for making compounds of structure B involving one or more reactions as follows:

1) converting a compound of formula I, or a salt or solvate thereof,

I

[Structure shown: HO—phenyl—$SO_3H$]

into a compound of formula II

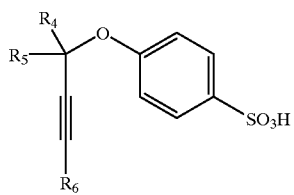

2) converting a compound of formula II above, or a salt or solvate thereof, to a compound of formula III:

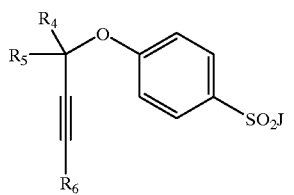

wherein J is fluorine, bromine, chlorine, 1,2,4-triazolyl, benzotriazolyl or imidazol-yl, and $R_4$, $R_5$ and $R_6$ are as defined above;

The invention is still further directed to a process for making compounds of structure B involving one or more reactions as follows:
1) converting phenol, or a salt or solvate thereof, into a compound of formula IV:

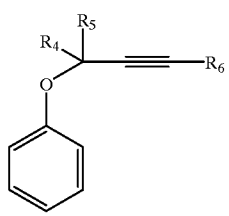

2) converting a compound of formula IV above, or a salt or solvate thereof, to a compound of formula II above.

Alkyl, alkenyl, alkynyl, and perfluoroalkyl include both straight chain as well as branched moieties. The definitions of alkyl, alkenyl, alkynyl, cycloalkyl and phenyl include alkyl, alkenyl, alkynyl, cycloalkyl and phenyl moieties which are unsubstituted (carbons bonded to hydrogen, or other carbons in the chain or ring) or may be mono- or poly-substituted with $R_7$. When a moiety contains more than substituent with the same designation (i.e., alkyl trisubstituted with $R_7$) each of those substituents ($R_7$ in this case) may be the same or different. Halogen means bromine, chlorine, fluorine, and iodine.

The compounds of this invention may contain an asymmetric carbon atom and some of the compounds of this invention may contain one or more asymmetric centers and may thus give rise to optical isomers and diastereomers. While shown without respect to stereochemistry, the present invention includes such optical isomers and diastereomers; as well as the racemic and resolved, enantiomerically pure R and S stereoisomers; as well as other mixtures of the R and S stereoisomers and pharmaceutically acceptable salts thereof. It is recognized that one optical isomer, including diastereomer and enantiomer, or stereoisomer may have favorable properties over the other. Thus when disclosing and claiming the invention, when one racemic mixture is disclosed, it is clearly contemplated that both optical isomers, including diastereomers and enantiomers, or stereoisomers substantially free of the other are disclosed and claimed as well.

Pharmaceutically acceptable salts can be formed from organic and inorganic acids, for example, acetic, propionic, lactic, citric, tartaric, succinic, fumaric, maleic, malonic, mandelic, malic, phthalic, hydrochloric, hydrobromic, phosphoric, nitric, sulfuric, methanesulfonic, naphthalenesulfonic, benzenesulfonic, toluenesulfonic, camphorsulfonic, and similarly known acceptable acids when a compound of this invention contains a basic moiety. Salts may also be formed from organic and inorganic bases, preferably alkali metal salts, for example, sodium, lithium, or potassium, when a compound of this invention contains an acidic moiety.

Preferred compounds of the invention are those having the formula:

B wherein B is:

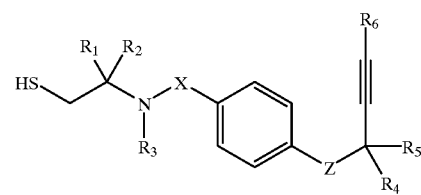

or a pharmaceutically acceptable salt thereof.

More preferred compounds of the invention are those in which B is:

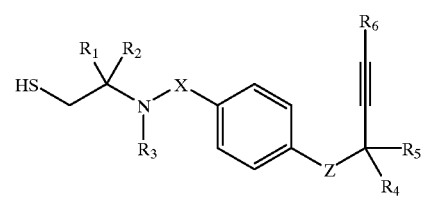

and X is $SO_2$; or a pharmaceutically acceptable salt thereof.

More preferred compounds of the invention are those in which B is:

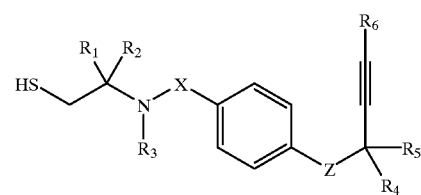

and X is $SO_2$, and Z is oxygen; or a pharmaceutically acceptable salt thereof.

More preferred compounds of the invention are those in which B is:

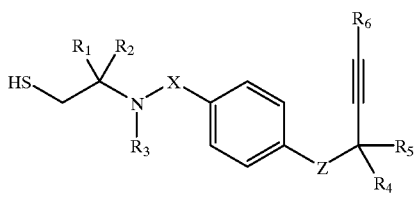

and X is SO$_2$, Z is oxygen and R$_4$ and R$_5$ are hydrogen; or a pharmaceutically acceptable salt thereof.

Still more preferred compounds of the invention are those in which B is:

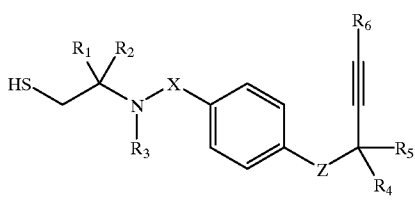

and X is SO$_2$, Z is oxygen, R$_4$ and R$_5$ are hydrogen, and R6 is —CH$_2$OH or methyl; or a pharmaceutically acceptable salt thereof.

Still more preferred compounds are those in which B is:

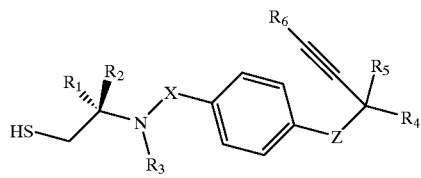

wherein R$_1$ is hydrogen, such that this compound has the absolute stereochemistry as shown in structure 1a above.

DETAILED DESCRIPTION OF THE INVENTION

The invention compounds are prepared using conventional techniques known to those skilled in the art of organic synthesis. The starting materials used in preparing the compounds of the invention are known, made by known methods or are commercially available.

Those skilled in the art will recognize that certain reactions are best carried out when other potentially reactive functionality on the molecule is masked or protected, thus avoiding undesirable side reactions and/or increasing the yield of the reaction. To this end, those skilled in the art may use protecting groups. Examples of these protecting group moieties may be found in T. W. Greene, P. G. M. Wuts "*Protective Groups in Organic Synthesis*", 2$^{nd}$ Edition, 1991, Wiley & Sons, New York. Reactive side chain functionalities on amino acid starting materials are preferably protected. The need and choice of protecting groups for a particular reaction is known to those skilled in the art and depends on the nature of the functional group to be protected (hydroxy, amino, carboxy, etc.), the structure and stability of the molecule of which the substituent is part and the reaction conditions. Those skilled in the art will recognize that the nature and order of the synthetic steps presented may be varied for the purpose of optimizing the formation of the compounds of the invention.

When preparing or elaborating compounds of the invention containing aryl, heteroaryl or heterocyclic rings, those skilled in the art recognize that substituents on that ring may be prepared before, after or concomitant with construction of the ring. For clarity, substituents on such rings have been omitted from the schemes herein below.

The thiol compounds of the invention, 1a–1c, are prepared according to Scheme 1 by converting an alcohol, 2, into the corresponding thioester or dithioester, 1b, via a Mitsunobu procedure using reagents such as triphenylphosphine, diethyl azodicarboxylate and thiolacetic acid. Conversion of 1b into thiol 1a is accomplished through hydrolysis or reductive cleavage of the ester using sodium methoxide, sodium borohydride or similar reagents. Thiol 1a may be converted into the corresponding disulfide using methods compatible with acetylenic substituents, such as oxidation with air or oxygen.

Alternatively, the alcohol moiety of 2 can be converted into a leaving group J, where J is a halide, tosylate, mesylate, triflate or similar functionality to give compound 3. Reaction of 3 with nucleophiles such as sodium sulfide, thiolacetic acid, dithiolacetic acid, or similar agents or their salts, then provides 1a or 1b.

Scheme 1

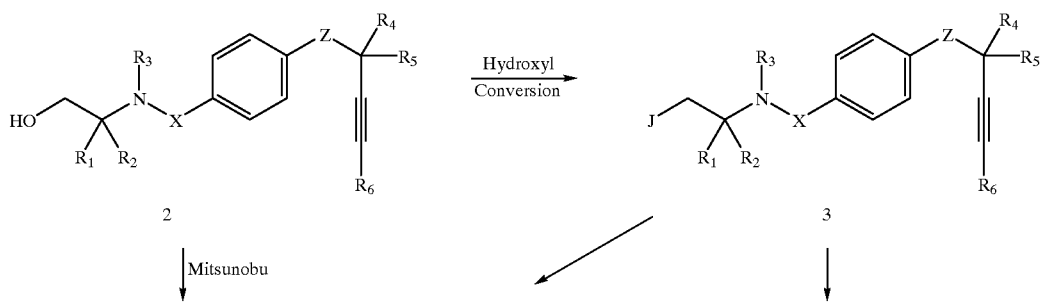

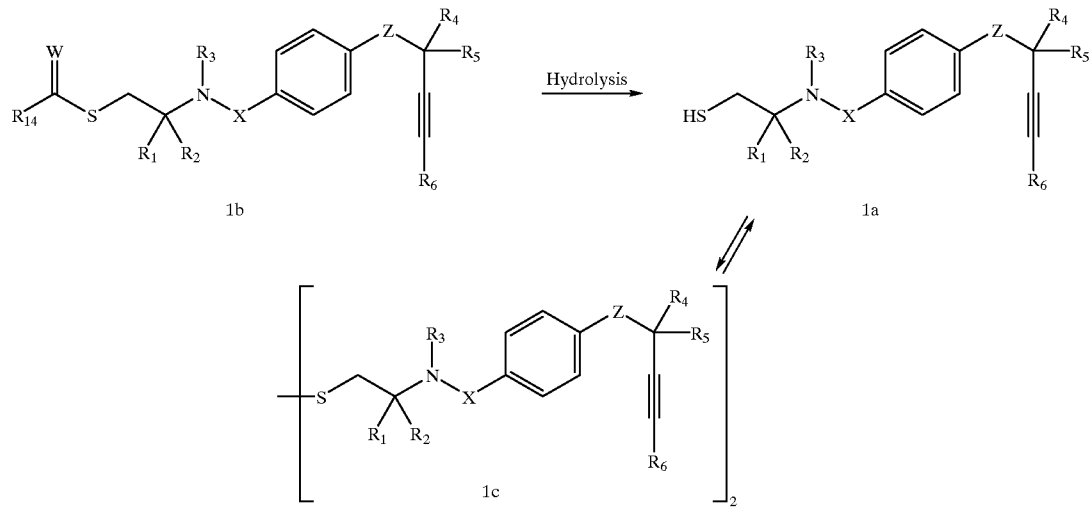

Alcohols 2 may be prepared as shown in Scheme 2. Amino-alcohol 4 ($R_{30}$=H), or its hydroxyl protected analog wherein $R_{30}$ is a suitable masking group such as trialkylsilyl or tetrahydropyran can be sulfonylated or phosphorylated with 7, wherein J is as described in Scheme 1, in the presence of a tertiary amine base, or pyridine, to provide 8. Alkylation of N—H compound 8 with $R_3J$ and a base such as potassium carbonate or sodium hydride in a polar aprotic solvent such as acetone, N,N-dimethylformamide (DMF), or tetrahydrofuran (THF) provides sulfonamide 9. Compound 9 is also available through direct reaction of 7 with an N-substituted amino-alcohol derivative, 5. Compound 5 is available via alkylation or reductive alkylation of amine 4, or by amination of 6 or the corresponding epoxide. Conversion of 9 into the alcohol is then performed in a manner consistent with the choice of protecting group $R_{30}$ and the presence of a carbon-carbon triple bond.

Scheme 2

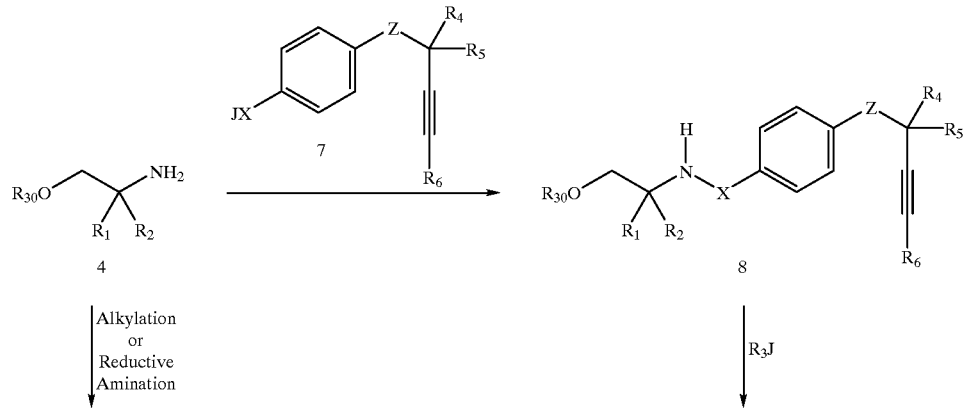

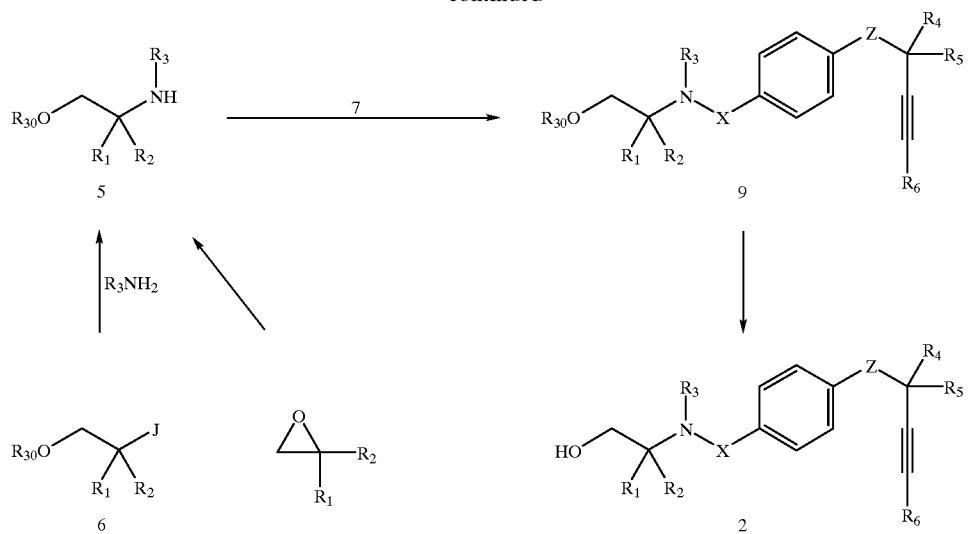

Another route to compounds 9 is shown in Scheme 3. Compound 7, for example the sulfonyl chloride, can react with a primary amine or ammonia to give compounds 10 or 11, respectively. Alkylation of 10 with 6 or an analogous epoxide provides 9 directly, whereas 11 can be aLkylated with $R_3J$ followed by 6 (or vice versa) or an epoxide to give 9.

by those skilled in the art. The sulfonic acid salts 14 may be converted into the corresponding sulfonyl chloride or other sulfonylating agent 7 by known methods, such as reaction with oxalyl chloride or other reagent compatible with substituents $R_4$, $R_5$ and $R_6$ and the acetylene. Alternatively, the disulfide 15 may be converted into di-acetylene 16 by reaction with compounds 13, followed by reduction of the Scheme 3

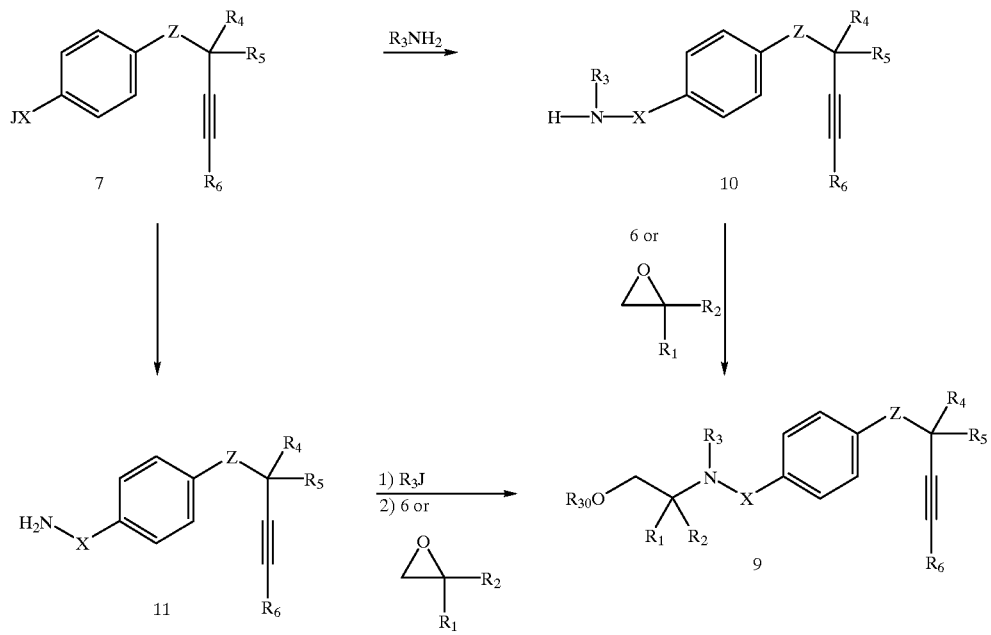

Methods of preparation of sulfonylating agents 7 are shown in Scheme 4. Thus, sulfonic acid salts 12, where $ZR_{50}$ is a hydroxy, thiol or substituted amino moiety may be alkylated with acetylenes 13, where J is a suitable leaving group such as halogen mesylate, tosylate, or triflate to give 14. Acetylenes 13 are commercially available or known compounds, or they may be synthesized by known methods disulfide bond to provide the analogous thiols which may be converted into 7 by known methods. Alkylation of the phenol, thiophenol, aniline or protected aniline 17 with 13 to give 18, followed by reaction with chlorosulfonic acid provide sulfonic acids 19 which are readily converted into 7 with oxalyl chloride or similar reagents. Thiophenols 20 are also precursors to 7 via protection of the thiol, alkylation of ZH, where Z is O, N or S, and deprotection of the sulfur followed by oxidation to the sulfonic acid 19.
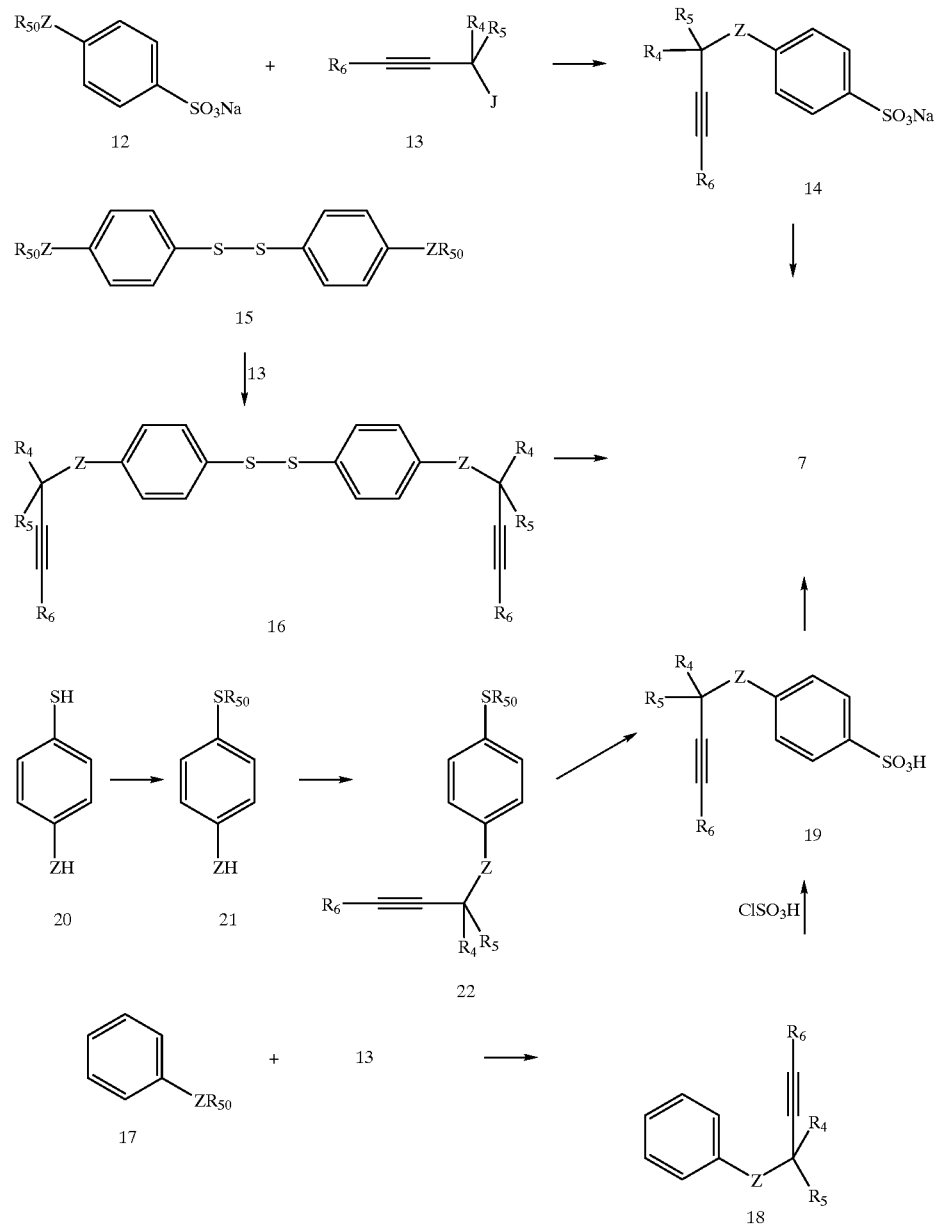
Scheme 4
The phosphorus containing analogs of 7 may be prepared using similar methodology, as shown in Scheme 5.

Scheme 5

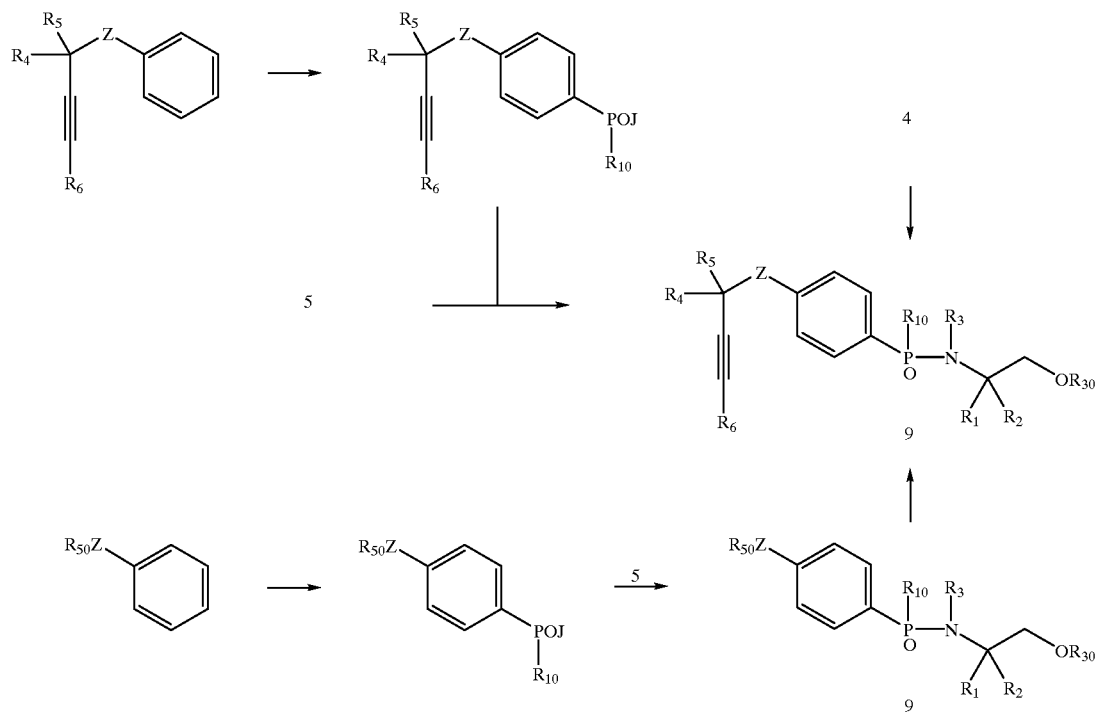

The acetylenic side chain may also be appended after sulfonylation or phosphorylation of the amino acid derivative, as shown in Scheme 6. Thus, the amino-alcohol derivatives 4 and 5 can be sulfonylated or phosphorylated with compounds 23, where $ZR_{50}$ is hydroxy or protected hydroxy, thiol or amine, and, if necessary, alkylated as in Scheme 2, to give 24. Removal of the $R_{50}$ masking group to give 25 and subsequent alkylation of the resulting phenol, thiol or amine with 13 provides 9. In the case where $ZR_{50}$ is equal to OH, no deprotection step is required to give 25. Alternatively, the $OR_{30}$ moiety of 24 may be converted into the analogous thioester, thiol or disulfide, as shown in Schemes 1 and 2, prior to deprotection of the $ZR_{50}$ moiety of compound 24. Subsequent alkylation of the unmasked —ZH group would then provide the compounds of the invention.

Scheme 6

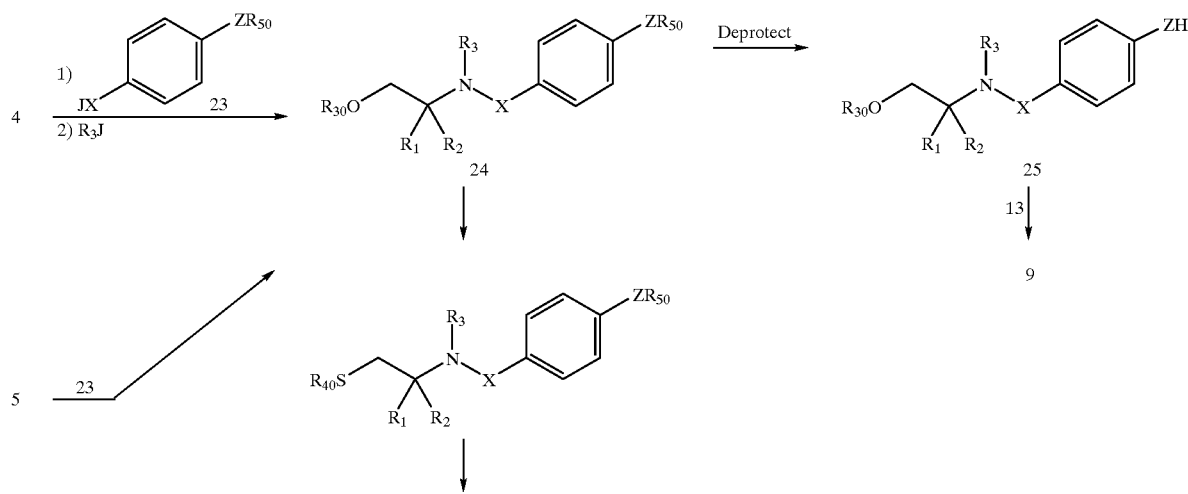

-continued

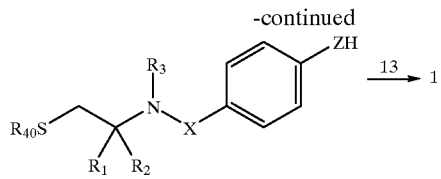

The propargylic amine analogs of 9 can be synthesized as shown in Scheme 7 starting from the amino-alcohol derivatives 4 and/or 5. Sulfonylation or phosphorylation with para-nitro aryl compound 26, for example 4-nitrobenzenesulfonyl chloride, followed by alkylation with $R_3J$ (for 4) using a base such as potassium carbonate or sodium hydride in DMF provides 27. Reduction of the nitro moiety with hydrogen and palladium on carbon, tin chloride or other known method to give aniline 28 and subsequent alkylation with 13 then provides 9. Aniline 28 may also be derivatized (29) prior to alkylation with 13 and then deprotected after the alkylation step. As in Scheme 6, compound 29 can first be converted into its thioester, disulfide or protected thiol analog, followed by appending the propargyl group, via alkylation with 13, and subsequent deprotection of the aniline to provide compounds 1a–1c of the invention.

displaced in a polar aprotic solvent with the propargylic derivative 33, where Z is O, S or NH, in the presence of a base such as sodium hydride, to give 9 directly. As described for Schemes 6 and 7 the order of synthetic operations may be changed such that the acetylenic moiety is appended after conversion of $OR_{30}$ into the corresponding thioester, disulfide or protected thiol.

Scheme 8

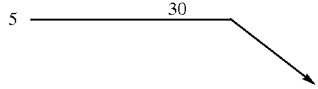

Scheme 7

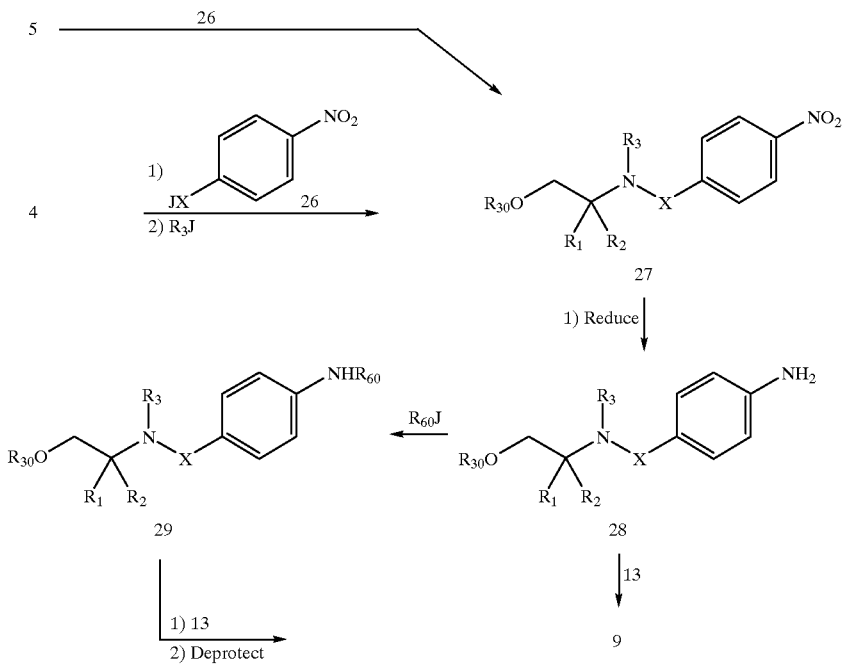

Acetylenic derivatives 9 are also accessible via the fluoro compounds 31, readily prepared from the amino-alcohol derivatives 4 and/or 5 by reaction with fluoroaryl 30, as shown in Scheme 8. Displacement of the fluorine of 31 in the presence of a base such as sodium hydride with a masked hydroxy, thiol, or amino group ($HZR_{70}$, where $R_{70}$ is a suitable protecting group) in a polar aprotic solvent such as DMF, followed by deprotection gives 32, which can then be alkylated with 13 to provide 9. Conversion of 31 to 32, where Z is sulfur, might also be accomplished with $Na_2S$, $K_2S$, NaSH or $KS(C=S)OEt$. The fluorine of 31 can also be -continued

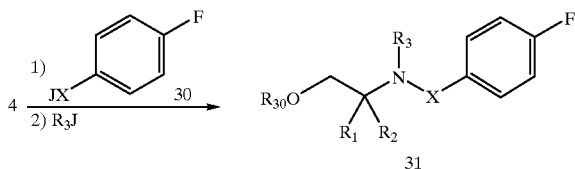

-continued

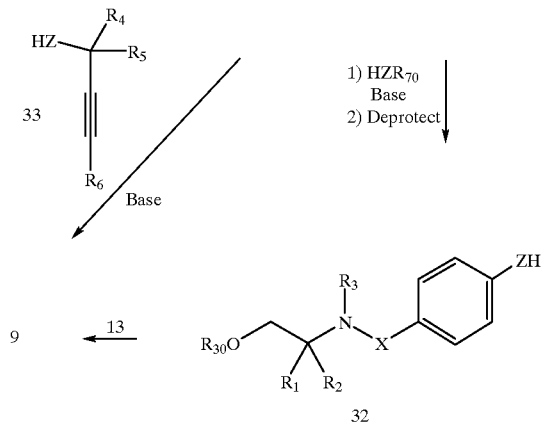

Compound 9, wherein Z is a methylene group, is available via 34, as shown in Scheme 9. Benzylic bromination of 34 with N-bromosuccinimide in a chlorinated hydrocarbon solvent provides bromide 35. This is followed by displacement of the bromide with the appropriate propynyl cuprate to provide sulfonamide 9.

Some of the methods available for the derivatization of compounds of structure 9 (for the case wherein $R_6$ is hydrogen) are shown in Scheme 10. Metallation of the terminal acetylene 9 followed by addition of an aldehyde or alkyl halide, sulfonate or triflate provides derivatives 36 and 37. Reaction of 9 with formaldehyde and an amine provides the Mannich addition product 38. Cyanogen bromide addition to 38 gives the propargylic bromide 39 which may be displaced with a variety of nucleophiles to give, for example, ethers, thioethers and amines, 40. Palladium catalyzed coupling reactions of 9 provide the aryl or heteroaryl acetylenes 41. It is recognized by those skilled in the art of organic synthesis that the successful use of these methods is dependent upon the compatibility of substituents on other parts of the molecule. Protecting groups and/or changes in the order of steps described herein may be required.

Scheme 9

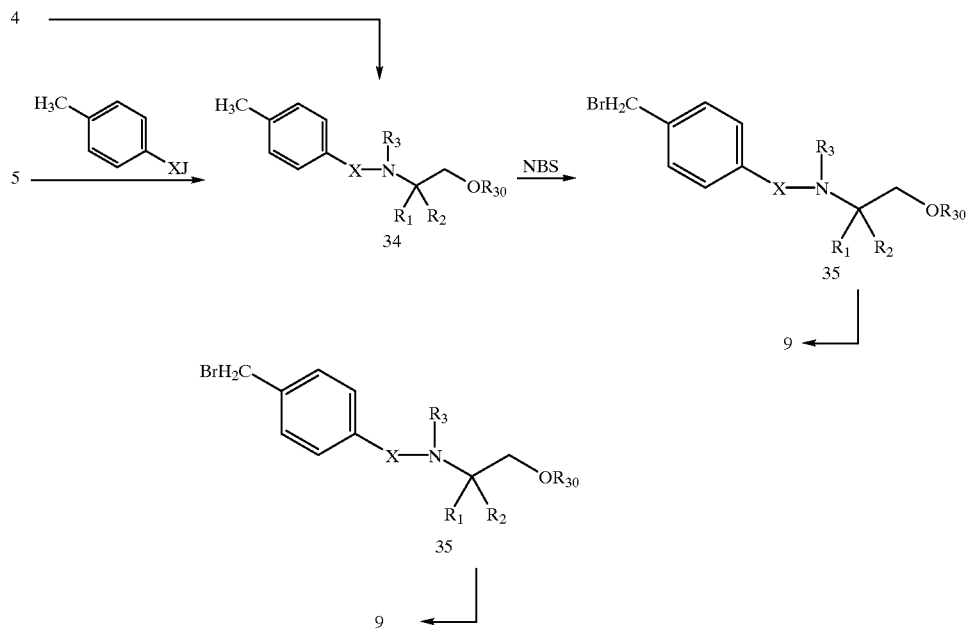

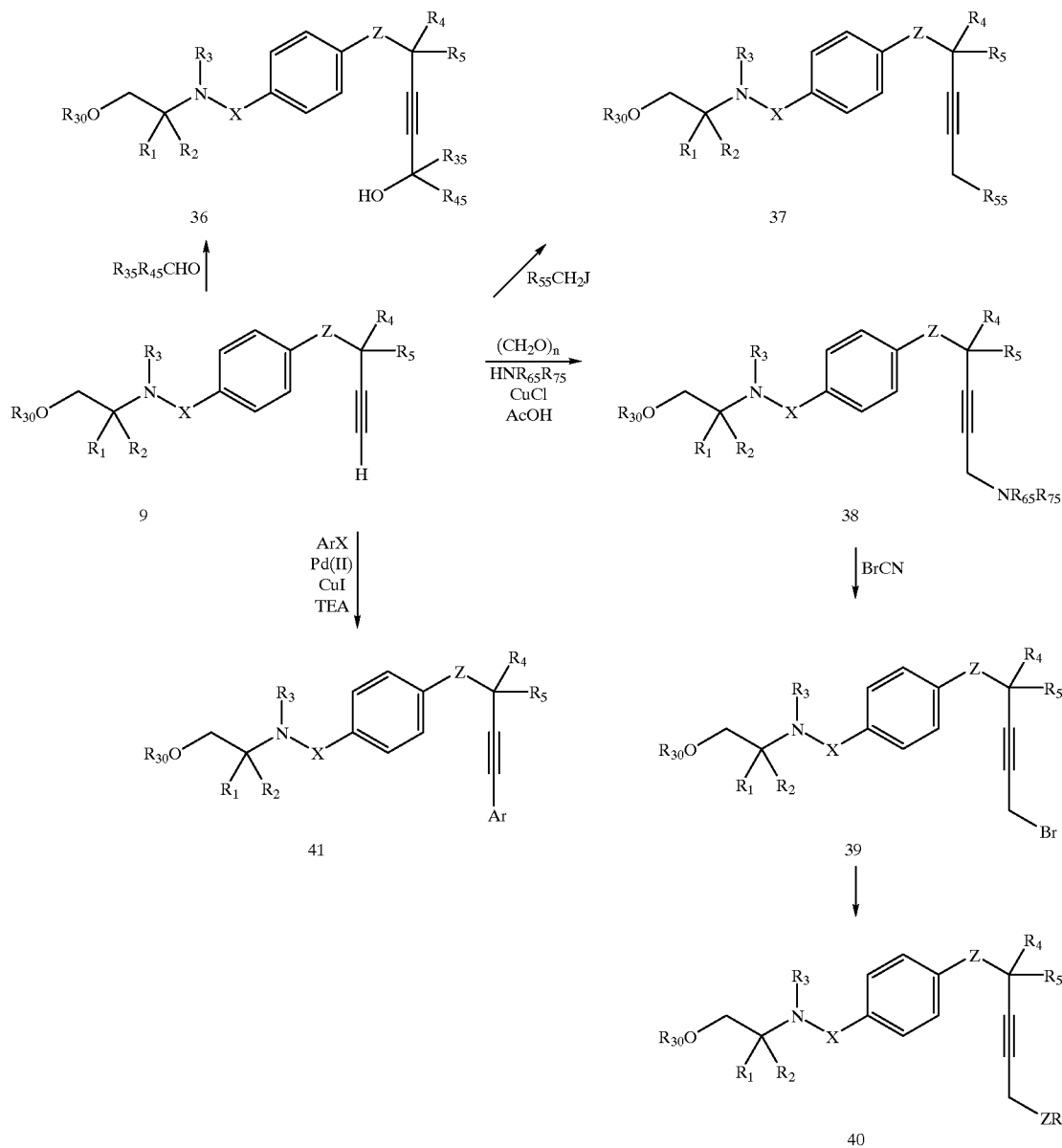

Scheme 10

The following specific examples illustrate the preparation of representative compounds of this invention. The starting materials, intermediates, and reagents are either commercially available or can be readily prepared following standard literature procedures by one skilled in the art of organic synthesis.

EXAMPLE 1

4-But-2,-ynyloxy-benzenesulfonic acid sodium salt

To a solution of 52.35 g (0.225 mol) of 4-hydroxybenzenesulfonate sodium salt in 1 L of isopropanol and 225 mL of a 1.0N solution of sodium hydroxide was added 59.96 g (0.45 mol) of 1-bromo-2-butyne. The resulting mixture was heated to 70° for 15 h and then the isopropanol was removed by evaporation in vacuo. The resulting white precipitate was collected by filtration, washed with isopropanol and ether and dried in vacuo to give 56.0 g (100%) of the butynyl ether as a white solid.

EXAMPLE 2

4-But-2-ynyloxy-benzenesulfonyl chloride

To a 0° solution of 43.8 mL (0.087 mol) of 2M oxalyl chloride/dichloromethane solution in 29 mL of dichloromethane was dropwise added 6.77 mL (0.087 mol) of DMF followed by 7.24 g (0.029 mol) of the product of Example 1. The reaction mixture was stirred for 10 minutes at 0° then let warm to room temperature and stirred for 2 days. The reaction was then poured into ice and extracted with 150 mL of hexanes. The organics were washed with water and brine, dried over $Na_2SO_4$, filtered and concentrated in vacuo to provide 6.23 g (88%) of the sulfonyl chloride as a yellow solid; m.p. 63–65° C. EI Mass Spec: 243.9 ($M^+$).

EXAMPLE 3

But-2-ynyloxy-benzene

To a solution of 6.14 g (0.023 mol) of triphenylphosphine dissolved in 100 mL of benzene and 40 mL of THF was added 1.75 mL (0.023 mol) of 2-butyn-1-ol. After five minutes 2.00 (0.023 mol) phenol, dissolved in 10 mL of THF, was added to the reaction followed by 3.69 mL (0.023 mol) of diethyl azodicarboxylate. The resulting reaction mixture was stirred for 18 h at room temperature and then concentrated in vacuo. The residue was chromatographed on silica gel eluting with ethyl acetate/hexanes (1:10) to provide 2.18 g (70%) of the butynyl ether as a clear liquid. EI Mass Spec: 146.0 MH+

EXAMPLE 4

4-But-2-ynyloxy-benzenesulfonyl chloride

To a solution of 0.146 g (1.0 mmol) of the product of Example 3 in 0.3 mL of dichloromethanein an acetone/ice bath under $N_2$ was dropwise added a solution of 0.073 mL (1.1 mmol) of chlorosulfonic acid in 0.3 mL of dichloromethane. After the addition was complete, the ice bath was removed and the reaction was stirred at room temperature for 2 h. To the reaction was then dropwise added 0.113 mL (1.3 mmol) of oxalyl chloride, followed by 0.015 mL DMF. The reaction was heated to reflux for 2 h and then diluted with hexane and poured into ice water. The organic layer was washed with brine, dried over sodium sulfate, and concentrated in vacuo to provide 0.130 mg (53%) of the desired product as a light brown solid.

EXAMPLE 5

4But-2-ynyloxy-N-(2-hydroxy-1-methyl-ethyl)-benzenesulfonamide

To a solution of 0.279 g (3.718 mmol) of (R)-(-)-2-amino-1-propanol in 2.6 mL of THF and 0.9 mL of water was added 0.62 mL of triethylamine followed by 1.00 g (4.09 mmol) of 4-but-2-ynyloxy-benzenesulfonyl chloride and the resulting mixture was stirred at room temperature for 15 h. The reaction was then diluted with ethyl acetate and washed with 5% HCl solution and water, dried over $MgSO_4$, filtered and concentrated in vacuo. The resulting solid was washed with ether and dried in vacuo to provide 0.873 g (83%) of the sulfonamide as a white solid. Electrospray Mass Spec: 283.8 $(M+H)^+$

EXAMPLE 6

4-But-2-ynyloxy-N-(2-hydroxy-1-methyl-ethyl)-N-methyl-benzenesulfonamide

To a solution of 0.400 g (1.413 mmol) of the product of Example 5 in 3.0 mL of DMF was added 0.585 g (4.240 mmol) of potassium carbonate followed by 0.132 mL (2.12 mmol) of iodomethane and the resulting mixture was stirred at room temperature for 12 h. The reaction was then diluted with ether and washed with water, dried over $MgSO_4$, filtered and concentrated in vacuo to provide 0.354 g (84%) of the N-methyl sulfonamide as a white solid. Electrospray Mass Spec: 297.9 $(M+H)^+$

EXAMPLE 7

Thioacetic acid S-{2-[(4-but-2-ynyloxy-benzenesulfonyl)-methyl-amino]-propyl}ester To a 0° C. solution of 0.302 g (1.017 mmol) of the product of Example 6 and 0.293 g (1.118 mmol) of triphenylphosphine in 4.0 mL of THF was added 0.176 mL (1.118 mmol) of diethyl azodicarboxylate. The resulting mixture was stirred for 0.5 h at 0° C. and then concentrated in vacuo. The residue was chromatographed on silica gel eluting with ethyl acetate/hexanes to provide 0.228 g (63%) of the thioacetate as a colorless oil. Electrospray Mass Spec: 355.9 $(M+H)^+$

EXAMPLE 8

4-But-2-ynyloxy-N-((1R)-2-mercapto-1-methyl-ethyl)-N-methyl-benzenesulfonamide To a solution of 0.168 g (0.473 mmol) of the product of Example 7 in 2.1 mL of methanol was added 0.092 g (1.704 mmol) of sodium methoxide. After stirring at room temperature for 2 h the reaction was quenched with 5% HCl solution and extracted with ether. The organics were dried opver Na2SO4, filtered and concentrated in vacuo. The residue was chromatographed on silica gel eluting with ethyl acetate/hexanes in a gradient from (1:10) to (1:3) to provide 0.148 g (100%) of the thiol as a colorless oil. Electrospray Mass Spec: 313.9 $(M+H)^+$

EXAMPLE 9

4-But-2-ynyloxy-N-(2-hydroxy-1-methyl-ethyl)-N-(2-morpholin-4-yl-ethyl)-benzenesulfonaniide According to the procedure of Example 6, 0.400 g (1.413 mmol) of the product of Example 5 and 0.289 g (1.555 mmol) of 4-(2-chloroethyl)morpholine hydrochloride provided 0.334 g (60%) of the N-morpholinoethyl sulfonamide as a colorless oil. Electrospray Mass Spec: 397.0 $(M+H)^+$

EXAMPLE 10

S-((2R)-2-{{[4-(2-Butynyloxy)phenyl]sulfonyl}[2-(4-morpholinyl)ethyl]amino}propyl)ethanethioate To a solution of 0.416 g (1.16 mmol) of the product of Example 9 in 4 mL of THF were added sequentially 0.304 g (1.16 mmol) of triphenylphosphine, 0.91 g (1.16 mmol) of diethyl azodicarboxylate and 0.25 mL (3.5 mmol) of thiolacetic acid. The reaction was stirred for 45 h, reduced to dryness and the resulting residue was subjected to flash chromatography eluting with ethyl acetate/hexanes (3:1) to provide 0.5 g (95%) of the thioacetate as a white solid. Electrospray Mass Spec: 455.3 $(M+H)^+$

EXAMPLE 11

4-(2-Butynyloxy)-N-[(1R)-1-methyl-2-sulfanylethyl]-N-[2-(4-morpholinyl)ethyl]benzenesulfonamide To a solution of 0.16 g (0.352 mmol) of the product of Example 10 in 2 mL of methanol in a sealable tube at −78° was added 20 mL of liquid ammonia. The tube was sealed and the reaction stirred for 12 h at room temperature. After recooling to −78° the reaction tube was unsealed and the solution was carefully reduced to dryness. The residue was chromatographed on silica gel eluting with methylene chloride/methanol (50:1) furnishing 121 mg (84%) of the desired thiol as a white solid. Electrospray Mass Spec: 413.4 $(M+H)^+$

EXAMPLE 12

(2R)-2-Amino-3-(tritylsulfanyl)propanamide

To 2.68 g (7.37 mmol) of S-trityl-L-cysteine and 40 mL of methanol was added 7 mL (96 mmol) of thionyl chloride dropwise. After heating at reflux for 6 h the solution was cooled to room temperature and then concentrated in vacuo. The resulting residue was taken up in 20 mL of methanol, treated with activated carbon, filtered and concentrated in vacuo yielding the methyl ester as an off-white foam. This material was dissolved in 6 mL of methanol in a sealable tube and cooled to −78°. After 30 mL of liquid ammonia was added, the tube was sealed and the reaction was stirred at room temperature for 14 h After recooling to −78° the reaction tube was unsealed and the solution was carefully reduced to dryness. The residue was chromatographed on silica gel eluting with methylene chloride/methanol (10:1) furnishing 1.52 g (57%) of the primary amide as a white solid. Electrospray Mass Spec: 363.2 (M+H)$^+$

EXAMPLE 13

(2R)-2-({[4-(2-Butynyloxy)phenyl]sulfonyl}amino)-3-(tritylsulfanyl)propanamide To a solution of 1.203 g (3.685 mmol) of the primary amide product from Example 12 and 1.39 mL (10 mmol) of triethylamine in 20 mL of methylene chloride was added in one portion 0.954 g (3.9 mmol) of 4-but-2-ynyloxy-benzenesulfonyl chloride. After stirring for 13 h, 50 mL of dichloromethane and 50 mL of water were added. The organic layer was washed with brine, dried over sodium sulfate, filtered, concentrated in vacuo and subjected to flash chromatography eluting with hexanes/ethyl acetate (1:1) to furnish 1.65 g (79%) of the desired sulfonamide as a white solid. Electrospray Mass Spec: 1139.6 (2M−H)$^−$

EXAMPLE 14

(2R)-2-{{[4-(2-Butnyloy)phenyl]sulfonyl}[2-(4-morpholinyl)ethyl]amino}-3-(tritylsulfanyl)propanamide To a solution of 0.6482 g (1.136 mmol) of the product from Example 13 in 3 mL of DMF was added 0.317 g (1.704 mmol) of 4-(2-chloroethyl)morpholine hydrochloride and 0.705 g (5.1 mmol) of potassium carbonate. The resulting mixture was heated at 60° for 14 h. After cooling to room temperature the reaction mixture was diluted with ethyl acetate and washed with water. The organic layer was dried over sodium sulfate, filtered, concentrated in vacuo and subjected to flash chromatography eluting with hexanes/ethyl acetate (1:5) to furnish 0.434 g (56%) of the desired compound as a white solid. Electrospray Mass Spec: 684.5 (M+H)$^+$

EXAMPLE 15

(2R)-2-{{[4-(2-Butynyloxy)phenyl]sulfonyl}[2-(4-morpholinyl)ethyl]amino}-3-sulfanylpropanamide To a solution of 0.116 g (0.170 mmol) of the product from Example 14 in 1.5 mL of methylene chloride was added triisopropylsilane, followed by trifluoroacetic acid. Upon consumption of starting material the solution was concentrated in vacuo and washed four times with 2 mL of ether. The residue was partitioned between ethyl acetate and saturated aqueous sodium bicarbonate. The organic layer was dried over sodium sulfate, filtered and concentrated in vacuo furnishing 66 mg (88%) of the thiol as a white solid. Electrospray Mass Spec: 442.4 (M+H)$^+$

PHARMACOLOGY

The ability of the compounds of the invention, or their pharmaceutically acceptable salts, to inhibit matrix metalloproteinases or TACE and, consequently, demonstrate their effectiveness for treating diseases modulated by matrix metalloproteinases or TACE is shown by the following in vitro assays.

Test Procedures for Measuring MMP-1, MMP-9, and MMP-13 Inhibition

These standard pharmacological test procedures are based on the cleavage of a thiopeptide substrates such as Ac-Pro-Leu-Gly(2-mercapto-4-methyl-pentanoyl)-Leu-Gly-OEt by the matrix metalloproteinases MMP-1, MMP-13 (collagenases) or MMP-9 (gelatinase), which results in the release of a substrate product that reacts colorimetrically with DTNB (5,5'-dithiobis(2-nitro-benzoic acid)). The enzyme activity is measured by the rate of the color increase. The thiopeptide substrate is made up fresh as a 20 mM stock in 100% DMSO and the DTNB is dissolved in 100% DMSO as a 100 mM stock and stored in the dark at room temperature. Both the substrate and DTNB are diluted together to 1 mM with substrate buffer (50 mM HEPES pH 7.5, 5 mM CaCl$_2$) before use. The stock of enzyme is diluted with buffer (50 mM HEPES, pH 7.5, 5 mM CaCl$_2$, 0.02% Brij) to the desired final concentration. The buffer, enzyme, vehicle or inhibitor, and DTNB/substrate are added in this order to a 96 well plate (total reaction volume of 200 μl) and the increase in color is monitored spectrophotometrically for 5 minutes at 405 nm on a plate reader and the increase in color over time is plotted as a linear line.

Alternatively, a fluorescent peptide substrate is used. In this test procedure, the peptide substrate contains a fluorescent group and a quenching group. Upon cleavage of the substrate by an MMP, the fluorescence that is generated is quantitated on the fluorescence plate reader. The assay is run in HCBC assay buffer (50 mM HEPES, pH 7.0, 5 mM Ca$^{+2}$, 0.02% Brij, 0.5% Cysteine), with human recombinant MMP-1, MMP-9, or MMP-13. The substrate is dissolved in methanol and stored frozen in 1 mM aliquots. For the assay, substrate and enzymes are diluted in HCBC buffer to the desired concentrations. Compounds are added to the 96 well plate containing enzyme and the reaction is started by the addition of substrate. The reaction is read (excitation 340 nm, emission 444 nm) for 10 min. and the increase in fluorescence over time is plotted as a linear line.

For either the thiopeptide or fluorescent peptide test procedures, the slope of the line is calculated and represents the reaction rate. The linearity of the reaction rate is confirmed ($r^2 > 0.85$). The mean (x±sem) of the control rate is calculated and compared for statistical significance ($p<0.05$) with drug-treated rates using Dunnett's multiple comparison test. Dose-response relationships can be generated using multiple doses of drug and IC$_{50}$ values with 95% CI are estimated using linear regression.

Test Procedure for Measuring TACE Inhibition

Using 96-well black microtiter plates, each well receives a solution composed of 10 μL TACE (final concentration 1 μg/mL), 70 μL Tris buffer, pH 7.4 containing 10% glycerol (final concentration 10 mM), and 10 μL of test compound solution in DMSO (final concentration 1 μM, DMSO concentration <1%) and incubated for 10 minutes at room temperature. The reaction is initiated by addition of a fluorescent peptidyl substrate (final concentration 100 μM) to each well and then shaking on a shaker for 5 sec.

The reaction is read (excitation 340 nm, emission 420 nm) for 10 min. and the increase in fluorescence over time is plotted as a linear line. The slope of the line is calculated and represents the reaction rate.

The linearity of the reaction rate is confirmed ($r^2>0.85$). The mean (x±sem) of the control rate is calculated and compared for statistical significance ($p<0.05$) with drug-treated rates using Dunnett's multiple comparison test. Dose-response relationships can be generate using multiple doses of drug and $IC_{50}$ values with 95% CI are estimated using linear regression.

Human Monocytic THP-1 Cell Differentiation Assay for Soluble Proteins (THP-1Soluble Protein Assay)

Mitogenic stimulation of THP-1 cells cause differentiation into macrophage like cells with concomitant secretion of tumor necrosis factor (TNF-α) and TNF receptor (TNF-R p75/80 and TNF-R p55/60) and Interleukin-8 (IL-8), among other proteins. In addition, non-stimulated THP-1 cells shed both the p75/80 and the p55/60 receptors over time. The release of membrane bound TNF-α and possibly TNF-R p75/80 and TNF-R p55/60, but not IL-8, is mediated by an enzyme called TNF-α converting enzyme or TACE. This assay can be used to demonstrate either an inhibitory or a stimulatory compound effect on this TACE enzyme and any cytotoxic consequence of such a compound.

THP-1 cells (from ATCC) are a human monocytic cell line which were obtained from the peripheral blood of a one year old male with acute monocytic leukemia. They can be grown in culture and differentiated into macrophage like cells by stimulation with mitogens.

For the assay, THP-1 cells are seeded from an ATCC stock which was previously grown and frozen back at 5×106 /ml/vial. One vial is seeded into a T25-flask with 16 mls of RPMI-1640 with glutamax (Gibco) media containing 10% fetal bovine serum, 100 units/ml penicillin, 100 μg/ml streptomycin, and $5 \times 10^{-5}$ M 2-mercapto-ethanol (THP-1 media). Each vial of cells are cultured for about two weeks prior to being used for an assay and then are used for only 4 to 6 weeks to screen compounds. Cells are subcultured on Mondays and Thursdays to a concentration of 1×105 /ml.

To perform an assay, the THP-1 cells are co-incubated in a 24 well plate with 50 ml/well of a 24 mg/ml stock of Lipopolysacharide (LPS) (Calbiochem Lot# B13189) at 37° C. in 5% $CO_2$ at a concentration of $1.091 \times 10^6$ cells/ml (1.1 ml/well) for a total of 24 hours. At the same time, 50 ml/well of drug, vehicle or THP-1 media is plated in appropriate wells to give a final volume of 1.2 ml/well. Standard and test compounds are dissolved in DMSO at a concentration of 36 mM and diluted from here to the appropriate concentrations in THP-1 media and added to the wells at the beginning of the incubation period to give final concentrations of 100 mM, 30 mM, 10 mM, 3 mM, 1 mM, 300 nM, and 100 nM. Cell exposure to DMSO was limited to 0.1% final concentration. Positive control wells were included in the experiment which had mitogen added but no drug. Vehicle control wells were included as well, which were identical to the positive control wells, except that DMSO was added to give a final concentration of 0.083%. Negative control wells were included in the experiment which had vehicle but no mitogen or drug added to the cells. Compounds can be evaluated for their effect on basal (non-stimulated) shedding of the receptors by replacing the LPS with 50 ml/well of THP-1 media. Plates are placed into an incubator set at 5% CO2 and at 37° C. After 4 hours of incubation, 300 ml/well of tissue culture supernatant (TCS) is removed for use in an TNF-α ELISA. Following 24 hours of incubation, 700 ml/well of TCS is removed and used for analysis in TNF-R p75/80, TNF-R p55/60 and IL-8 ELISAs.

In addition, at the 24 hours timepoint, and the cells for each treatment group are collected by resuspension in 500 μl/well of THP-1 media and transferred into a FACS tube. Two ml/tube of a 0.5 mg/ml stock of propidium iodide (PI) (Boerhinger Mannheim cat. # 1348639) is added. The samples are run on a Becton Dickinson FaxCaliber FLOW cytometry machine and the amount of dye taken up by each cell is measured in the high red wavelength (FL3). Only cells with compromised membranes (dead or dying) can take up PI. The percent of live cells is calculated by the number of cells not stained with PI, divided by the total number of cells in the sample. The viability values calculated for the drug treated groups were compared to the viability value calculated for the vehicle treated mitogen stimulated group ("vehicle positive control") to determine the "percent change from control". This "percent change from control" value is an indicator of drug toxicity.

The quantity of soluble TNF-α, TNF-R p75/80 and TNF-R p55/60 and IL-8 in the TCS of the THP-1 cell cultures are obtained with commercially available ELISAs from R&D Systems, by extrapolation from a standard curve generated with kit standards. The number of cells that either take up or exclude PI are measured by the FLOW cytometry machine and visualized by histograms using commercially available Cytologic software for each treatment group including all controls.

Biological variability in the magnitude of the response of THP-1 cell cultures requires that experiments be compared on the basis of percent change from "vehicle positive control" for each drug concentration. Percent change in each soluble protein evaluated from the "vehicle positive control" was calculated for each compound concentration with the following formula:

$$\% \text{ Change} = \frac{\text{pg/ml (compound)} - \text{pg/ml (veh pos control)}}{\text{pg/ml (veh pos control)} - \text{pg/ml (veh neg control)}} \times 100$$

For the soluble protein (TNF-α, p75/80, p55/60, IL-8) studies under stimulated conditions, the mean pg/ml of duplicate wells were determined and the results expressed as percent change from "vehicle positive control". For the soluble protein (p75/80 and p55/60 receptors) studies under non-stimulated conditions, the mean pg/ml of duplicate wells were determined and the results expressed as percent change from "vehicle positive control" utilizing the following formula:

$$\% \text{ Change} = \frac{\text{pg/ml (compound neg control)} - \text{pg/ml (veh neg control)}}{\text{pg/ml (veh neg control)}} \times 100$$

$IC_{50}$ values for each compound are calculated by non-linear regression analysis using customized software utilizing the JUMP statistical package.

For the cell viability studies, the viabilities (PI exclusion) of pooled duplicate wells were determined and the results expressed as % change from "vehicle positive control". The viability values calculated for the compound treated groups were compared to the viability value calculated for the "vehicle positive control" to determine "percent change from control" as below. This value "percent change from control" is an indicator of drug toxicity.

$$\% \text{ Change} = \frac{\% \text{ live cells (compound)}}{\% \text{ live cells (veh pos control)}} - 1 \times 100$$

References

Bjomberg, F., Lantz, M., Olsson, I., and Gullberg, U. Mechanisms involved in the processing of the p55 and the p75 tumor necrosis factor (TNF) receptors to soluble receptor forms. Lymphokine Cytokine Res. 13:203–211, 1994.

Gatanaga, T., Hwang, C., Gatanaga, M., Cappuccini, F., Yamamoto, R., and Granger, G. The regulation of TNF mRNA synthesis, membrane expression, and release by PMA- and LPS-stimulated human monocytic THP-1 cells in vitro. Cellular Immun. 138:1–10, 1991.

Tsuchiya, S., Yamabe, M., Yamagughi, Y., Kobayashi, Y., Konno, T., and Tada, K. Establishment and characterization of a human acute monocytic leukemia cell line (THP-1). Int. J. Cancer. 26:1711–176, 1980.

Results of the above in vitro matrix metalloproteinase inhibition, TACE inhibition and THP standard pharmacological test procedures are given in Table 1 below.

Applicable solid carriers can include one or more substances which may also act as flavoring agents, lubricants, solubilizers, suspending agents, fillers, glidants, compression aids, binders or tablet-disintegrating agents or an encapsulating material. In powders, the carrier is a finely divided solid which is in admixture with the finely divided active ingredient. In tablets, the active ingredient is mixed with a carrier having the necessary compression properties in suitable proportions and compacted in the shape and size desired. The powders and tablets preferably contain up to 99% of the active ingredient. Suitable solid carriers include, for example, calcium phosphate, magnesium stearate, talc, sugars, lactose, dextrin, starch, gelatin, cellulose, methyl cellulose, sodium carboxymethyl cellulose, polyvinylpyrrolidine, low melting waxes and ion exchange resins.

Liquid carriers may be used in preparing solutions, suspensions, emulsions, syrups and elixirs. The active ingredient of this invention can be dissolved or suspended in a pharmaceutically acceptable liquid carrier such as water, an organic solvent, a mixture of both or pharmaceutically acceptable oils or fat. The liquid carrier can contain other suitable pharmaceutical additives such a solubilizers,

TABLE 1

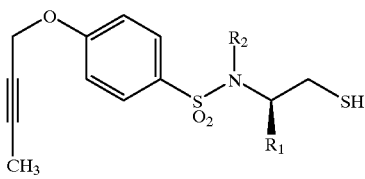

| Example # | $R_1$ | $R_2$ | MMP-1[a] | MMP-9[a] | MMP-13[a] | TACE[a] | THP |
|---|---|---|---|---|---|---|---|
| 8 | $CH_3$ | $CH_3$ | 6,300 | 2,700 | 679 | 273 | 3 |
| 11 | $CH_3$ | $(CH_2)_2$Morph | — | — | — | 362 | 11 |
| 15 | $CONH_2$ | $(CH_2)_2$Morph | — | — | — | 263 | 19 |

[a]$IC_{50}$ (nM)

Based on the standard pharmacological test procedures described above, the compounds of this invention are useful in the treatment of disorders such as arthritis, tumor metastasis, tissue ulceration, abnormal wound healing, periodontal disease, graft rejection, insulin resistance, bone disease and HIV infection.

The compounds of this invention are also useful in treating or inhibiting pathological changes mediated by matrix metalloproteinases such as atherosclerosis, atherosclerotic plaque formation, reduction of coronary thrombosis from atherosclerotic plaque rupture, restenosis, MMP-mediated osteopenias, inflammatory diseases of the central nervous system, skin aging, angiogenesis, tumor metastasis, tumor growth, osteoarthritis, rheumatoid arthritis, septic arthritis, corneal ulceration, proteinuria, aneurysmal aortic disease, degenerative cartilage loss following traumatic joint injury, demyelinating diseases of the nervous system, cirrhosis of the liver, glomerular disease of the kidney, premature rupture of fetal membranes, infammatory bowel disease, age related macular degeneration, diabetic retinopathy, proliferative vitreoretinopathy, retinopathy of prematurity, ocular inflammation, keratoconus, Sjogren's syndrome, myopia, ocular tumors, ocular angiogenesis/neovascularization and corneal graft rejection.

Compounds of this invention may be administered neat or with a pharmaceutical carrier to a patient in need thereof. The pharmaceutical carrier may be solid or liquid.

emulsifiers, buffers, preservatives, sweeteners, flavoring agents, suspending agents, thickening agents, colors, viscosity regulators, stabilizers or osmo-regulators. Suitable examples of liquid carriers for oral and parenteral administration include water (particularly containing additives as above, e.g., cellulose derivatives, preferable sodium carboxymethyl cellulose solution), alcohols (including monohydric alcohols and polyhydric alcohols, e.g., glycols) and their derivatives, and oils (e.g., fractionated coconut oil and arachis oil). For parenteral administration the carrier can also be an oily ester such as ethyl oleate and isopropyl myristate. Sterile liquid carriers are used in sterile liquid form compositions for parenteral administration.

Liquid pharmaceutical compositions which are sterile solutions or suspensions can be utilized by, for example, intramuscular, intraperitoneal or subcutaneous injection. Sterile solutions can also be administered intravenously. Oral administration may be either liquid or solid composition form.

The compounds of this invention may be administered rectally in the form of a conventional suppository. For administration by intranasal or intrabronchial inhalation or insufflation, the compounds of this invention may be formulated into an aqueous or partially aqueous solution, which can then be utilized in the form of an aerosol. The compounds of this invention may also be administered transdermally through the use of a transdermal patch containing the active compound and a carrier that is inert to the active compound, is non-toxic to the skin, and allows delivery of the agent for systemic absorption into the blood stream via the skin. The carrier may take any number of forms such as creams and ointments, pastes, gels, and occlusive devices. The creams and ointments may be viscous liquid or semi-solid emulsions of either the oil in water or water in oil type. Pastes comprised of absorptive powders dispersed in petroleum or hydrophilic petroleum containing the active ingredient may also be suitable. A variety of occlusive devices may be used to release the active ingredient into the blood stream such as a semipermeable membrane covering a reservoir containing the active ingredient with or without a carrier, or a matrix containing the active ingredient. Other occlusive devices are known in the literature.

The dosage to be used in the treatment of a specific patient suffering a MMP or TACE dependent condition must be subjectively determined by the attending physician. The variables involved include the severity of the dysfunction, and the size, age, and response pattern of the patient. Treatment will generally be initiated with small dosages less than the optimum dose of the compound. Thereafter the dosage is increased until the optimum effect under the circumstances is reached. Precise dosages for oral, parenteral, nasal, or intrabronchial administration will be determined by the administering physician based on experience with the individual subject treated and standard medical principles.

Preferably the pharmaceutical composition is in unit dosage form, e.g., as tablets or capsules. In such form, the composition is sub-divided in unit dose containing appropriate quantities of the active ingredient; the unit dosage form can be packaged compositions, for example packed powders, vials, ampoules, prefilled syringes or sachets containing liquids. The unit dosage form can be, for example, a capsule or tablet itself, or it can be the appropriate number of any such compositions in package form.

What is claimed:

1. The invention provides TACE and MMP inhibitors having the formula:

B wherein B is

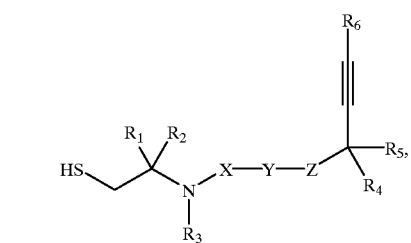

1a

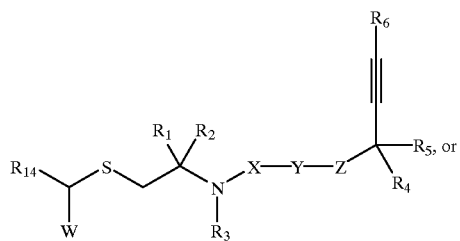

1b

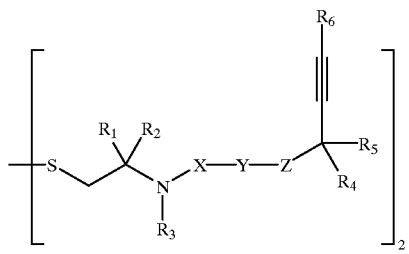

1c wherein:

W is oxygen or sulfur;

X is $SO_2$ or —P(O)—$R_{10}$;

Y is aryl or heteroaryl as defined below, with the proviso that X and Z may not be bonded to adjacent atoms of Y;

Z is O, NH, $CH_2$ or S;

$R_1$ is hydrogen, aryl, alkyl of 1–6 carbon atoms, alkenyl of 2–6 carbon atoms, alkynyl of 2–6 carbon atoms;

$R_2$ is hydrogen, aryl or heteroaryl as defined below, cycloalkyl of 3–6 carbon atoms, —C4–C8-cycloheteroalkyl, alkyl of 1–6 carbon atoms, alkenyl of 2–6 carbon atoms, alkynyl of 2–6 carbon atoms, or $CONR_8R_9$;

or $R_1$ and $R_2$, together with the atom to which they are attached, may form a ring wherein $R_1$ and $R_2$ represent a divalent moiety of the formula:

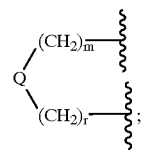

wherein

Q=a carbon-carbon single or double bond, O, S, SO, —N—$R_{11}$, or —$CONR_{15}$;

m=1–3;

r=1 or 2, with the proviso that when Q is a bond, r is equal to 2;

Aryl is phenyl or naphthyl optionally substituted by one to two substituents selected from $R_7$, where $R_7$ is as defined below;

Heteroaryl is defined as

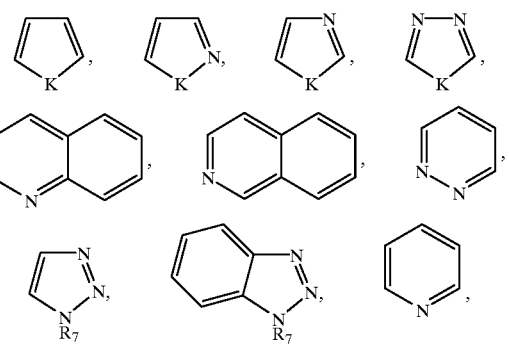

optionally mono- or di- substituted by $R_7$, wherein K is defined as O, S or —$NR_{15}$;

$R_3$ is hydrogen or alkyl of 1–6 carbon atoms;

or $R_1$ and $R_3$, together with the atoms to which they are attached, may form a 5 to 8 membered ring wherein $R_1$ and $R_3$ represent divalent moieties of the formulae:

wherein

Q and m are as defined above;

A is aryl or heteroaryl;

s is 0–3;

u is 1–4;

$R_4$ and $R_5$ are each, independently, hydrogen, alkyl of 1–6 carbon atoms, —CN, —CCH;

$R_6$ is hydrogen, aryl, heteroaryl, alkyl of 1–6 carbon atoms, alkenyl of 2–6 carbon atoms, alkynyl of 2–6 carbon atoms, cycloalkyl of 3–6 carbon atoms or —C4–C8-cycloheteroalkyl as defined below;

$R_7$ is hydrogen, halogen, alkyl of 1–6 carbon atoms; alkenyl of 2–6 carbon atoms; alkynyl of 2–6 carbon atoms, cycloalkyl of 3–6 carbon atoms, —$OR_8$, —CN, —$COR_8$, perfluoroalkyl of 1–4 carbon atoms, —O-perfluoroalkyl of 1–4 carbon atoms, —$CONR_8R_9$, —$S(O)_nR_8$, —$OPO(OR_8)OR_9$, —$PO(OR_8)R_9$, —$OC(O)NR_8R_9$, —$C(O)NR_8OR_9$, —$COOR_8$, —$SO_3H$, —$NR_8R_9$, —$N[(CH_2)_2]_2NR_8$, —$NR_8COR_9$, —$NR_8COOR_9$, —$SO_2NR_8R_9$, —$NO_2$, —$N(R_8)SO_2R_9$, —$NR_8CONR_8R_9$, —$NR_8C(=NR_9)NR_8R_9$, -tetrazol-5-yl, —$SO_2NHCN$, —$SO_2NHCONR_8R_9$, phenyl, heteroaryl as defined above, or —C4–C8-cycloheteroalkyl as defined below;

wherein —$NR_8R_9$ may form a pyrrolidine, piperidine, morpholine, thiomorpholine, oxazolidine, thiazolidine, pyrazolidine, piperazine, or azetidine ring;

wherein —C4–C8-cycloheteroalkyl is defined as wherein K is defined as above;

$R_8$ and $R_9$ are each, independently, hydrogen, alkyl of 1–6 carbon atoms, cycloalkyl of 3–6 carbon atoms, aryl, heteroaryl or —C4–C8-cycloheteroalkyl;

$R_{10}$ is alkyl of 1–6 carbon atoms, cycloalkyl of 3–6 carbon atoms, aryl or heteroaryl as defined above;

$R_{11}$ is hydrogen, alkyl of 1–6 carbon atoms, cycloalkyl of 3–6 carbon atoms, aryl, heteroaryl, —$S(O)_nR_8$, —$COOR_8$, —$CONR_8R_9$, —$SO_2NR_8R_9$ or —$COR_8$;

$R_{12}$ and $R_{13}$ are independently selected from H, —$OR_8$, —$NR_8R_9$, alkyl of 1–6 carbon atoms, alkenyl of 2–6 carbon atoms, alkynyl of 2–6 carbon atoms, cycloalkyl of 3–6 carbon atoms, aryl, heteroaryl, —$COOR_8$; —$CONR_8R_9$; or $R_{12}$ and $R_{13}$ together form a —C3–C6-cycloalkyl of 3–6 carbon atoms or a —C4–C8-cycloheteroalkyl ring; or $R_{12}$ and $R_{13}$ together with the carbon to which they are attached, form a carbonyl group;

with the proviso that $R_{10}$ and $R_{12}$ or $R_{11}$ and $R_{12}$ may form a cycloheteroalkyl ring, wherein cycloheteroalkyl is as defined above, when they are attached to adjacent atoms;

$R_{14}$ is —$OR_8$, —$NR_8R_9$, alkyl of 1–6 carbon atoms, cycloalkyl of 3–6 carbon atoms, aryl or heteroaryl;

$R_{15}$ is hydrogen, aryl, heteroaryl, alkyl of 1–6 carbon atoms or cycloalkyl of 3–6 carbon atoms;

and n is 0–2;

or a pharmaceutically acceptable salt thereof.

2. A compound according to claim 1 wherein B is

1a or a pharmaceutically acceptable salt thereof.

3. A compound according to claim 2 wherein X is $SO_2$; or a pharmaceutically acceptable salt thereof.

4. A compound according to claim 2 wherein X is $SO_2$, and Z is oxygen; or a pharmaceutically acceptable salt thereof.

5. A compound according to claim 2 wherein X is $SO_2$, Z is oxygen and $R_4$ and $R_5$ are hydrogen; or a pharmaceutically acceptable salt thereof.

6. A compound according to claim 2 wherein X is $SO_2$, Z is oxygen, $R_4$ and $R_5$ are hydrogen, and R6 is —$CH_2OH$ or methyl; or a pharmaceutically acceptable salt thereof.

7. A compound according to claim 1 wherein $R_1$ is hydrogen, such that this compound has the absolute stereochemistry as shown in structure 1a below.

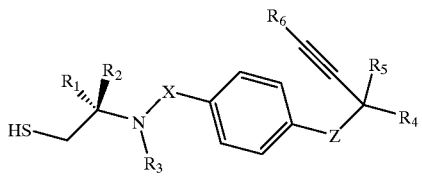

8. A method of inhibiting pathological changes mediated by TNF-α converting enzyme (TACE) in a mammal in need thereof which comprises administering to said mammal a therapeutically effective amount of a compound having the formula according to claim 1.

9. The method according to claim 8 wherein the condition treated is rheumatoid arthritis, graft rejection, cachexia, inflammation, fever, insulin resistance, septic shock, congestive heart failure, inflammatory disease of the central nervous system, inflammatory bowel disease or HIV infection.

10. A pharmaceutical composition comprising a compound having the formula according to claim 1.

11. A compound according to claim 1 which is 4-But-2-ynyloxy-N-((1R)-2-mercapto-1-methyl-ethyl)-N-methylbenzene-sulfonamide.

12. A compound of claim 1 which is (2R)-2-{{[4-(2-Butynyloxy)phenyl]sulfonyl}[2-(4-morpholinyl)ethyl]amino}-3-sulfanylpropanamide.

13. A compound of claim 1 which is 4-(2-Butynyloxy)-N-[(1R)-1-methyl-2-sulfanylethyl]-N-[2-(4-morpholinyl)ethyl]benzenesulfonaniide.

* * * * *